(12) United States Patent
Fu et al.

(10) Patent No.: US 10,214,552 B2
(45) Date of Patent: Feb. 26, 2019

(54) METHOD FOR PURIFYING BETA-NICOTINAMIDE MONONUCLEOTIDE

(71) Applicant: BONTAC BIO-ENGINEERING (SHENZHEN) CO., LTD, Shenzhen (CN)

(72) Inventors: Rongzhao Fu, Shenzhen (CN); Zhu Dai, Shenzhen (CN); Qi Zhang, Shenzhen (CN)

(73) Assignee: BONTAC BIO-ENGINEERING (SHENZHEN) CO., LTD., Shenzhen (CN)

( * ) Notice: Subject to any disclaimer, the term of this patent is extended or adjusted under 35 U.S.C. 154(b) by 185 days.

(21) Appl. No.: 15/110,005

(22) PCT Filed: Dec. 2, 2015

(86) PCT No.: PCT/CN2015/096215
§ 371 (c)(1),
(2) Date: Jul. 6, 2016

(87) PCT Pub. No.: WO2016/086860
PCT Pub. Date: Jun. 9, 2016

(65) Prior Publication Data
US 2016/0333041 A1    Nov. 17, 2016

(30) Foreign Application Priority Data
Mar. 16, 2015   (CN) .......................... 2015 1 0113667

(51) Int. Cl.
*C07H 19/20*   (2006.01)
*C07H 1/06*   (2006.01)
*C07H 19/048*   (2006.01)

(52) U.S. Cl.
CPC .............. *C07H 1/06* (2013.01); *C07H 19/048* (2013.01)

(58) Field of Classification Search
CPC ................................. C07H 1/06; C07H 19/048
See application file for complete search history.

(56) References Cited

U.S. PATENT DOCUMENTS

| 4,411,995 A | 10/1983 | Whitesides et al. |
| 4,622,294 A * | 11/1986 | Kung .................. G01N 33/532 435/14 |
| 4,783,400 A * | 11/1988 | Canova-Davis ..... G01N 33/532 435/14 |

FOREIGN PATENT DOCUMENTS

| CN | 104817604 | 8/2015 |
| JP | 45000948 | 1/1970 |

OTHER PUBLICATIONS (R) Yamada et al., "The Simultaneous Measurement of Nicotinamide Adenine Dinucleotide and Related Compounds by Liquid Chromatography/Electrospray Ionization Tandem Mass Spectrometry," Analytical Biochemistry, 352(2), 282-285 (2006).*
International Search Report for International Application No. PCT/CN2015/096215 dated Mar. 18, 2016, with English translation, total 5 pages.
Preiss et al. "Enzymatic synthesis of nicotinamide mononucleotide", The Journal of Biological Chemistry, Apr. 1957, 225(2), pp. 759-770, total 13 pages.
Hensel et al., abstract of "Convenient method for preparation and purification of nicotinamide mononucleotide analogs", Analytical Biochemistry, vol. 68, Issue 1, Sep. 1975.
Friedmann, abstract of "Preparation of DPN+ and NMN labeled with14C in the pyridine moiety", Methods in Enzymology, vol. 18, Part B, 1971.

* cited by examiner

*Primary Examiner* — Lawrence E Crane
(74) *Attorney, Agent, or Firm* — Hamre, Schumann, Mueller & Larson, P.C.

(57) ABSTRACT

A method for purifying β-nicotinamide mononucleotide (NMN) includes: sequentially microfiltrating and nanofiltrating a crude product solution containing NMN using membrane concentration devices to obtain a concentrated crude product solution; adjusting the concentrated crude product solution to pH 3-7 to obtain a loading solution, loading the loading solution onto a preparative reverse phase high performance liquid chromatographic column, and purifying by gradient elution using an octadecylsilane-bonded silica gel as a stationary phase, a hydrochloric acid solution at pH 3-7 as a mobile phase A, and 100% ethanol as a mobile phase B, to obtain a purified sample solution; concentrating the purified sample solution by nanofiltration and freeze drying in a vacuum freeze drier to obtain a purified NMN.

9 Claims, No Drawings

METHOD FOR PURIFYING BETA-NICOTINAMIDE MONONUCLEOTIDE

BACKGROUND

Technical Field

The present invention relates to a method for purifying a nucleotide coenzyme, and particularly to a method for purifying β-nicotinamide mononucleotide.

Related Art

β-nicotinamide mononucleotide (NMN) is a substrate for synthesizing coenzyme I, and becomes coenzyme I (NAD) after adenylation in the presence of a nicotinamide nucleotide adenylyltransferase. The level of NMN and the activity of nicotinamide nucleotide adenylyltransferase (NAMPT) in organisms have a direct influence on the NAD concentration. Moreover, NMN is directly involved in the transfer of adenosine in vivo, and is an important substrate for synthesis and an important function modulating substance in organisms. In term of the therapeutic application, NMN can be used for anti-aging and for treatment of chronic diseases. Research suggests that NMN plays a role in the regulation of insulin secretion, and affects the level of mRNA expression. Therefore, NMN has a broad application prospect in medicine, and also a promising market prospect as a reactive substrate in the chemical industry.

NMN is generally purified by using ion exchange resins (Hensel et al., *Analytical Biochemistry*, Vol. 68 (1), 1975, 128-137; Friedmann,*Methods in Enzymology*, Vol. 18, 1971, 51-55). Due to a variety of analogues thereof having extremely similar charges and polarities, such as NAD, the separation and purification is quite difficult, and the analogue impurities contained therein cannot be radically removed. As a result, the product purity attained through ion exchange is only about 60%, and the yield is only 40%. Therefore, the production efficiency is low, and the method is not suitable for use in large-scale production.

Therefore, improvements and developments are needed in the art.

SUMMARY

Technical Problem

In view of the defects existing in the prior art, an object of the present invention is to provide a method for purifying β-nicotinamide mononucleotide, for the purpose of addressing the problems of difficulty in complete removal of other analogues having similar charges and polarities during the purification process of β-nicotinamide mononucleotide, and low purity and low yield of the product.

Technical Solution

To achieve the above object, the following technical solution is adopted in the present invention.

A method for purifying β-nicotinamide mononucleotide comprises the steps of:

a. sequentially microfiltrating and nanofiltrating a pretreated β-nicotinamide mononucleotide solution with membrane concentration devices, to collect a concentrated crude product solution;

b. adjusting the obtained crude product solution to pH 3-7, loading it onto a preparative reverse phase high performance liquid chromatographic column, and purifying by gradient elution using an octadecylsilane-bonded silica gel as a stationary phase, a hydrochloric acid solution at pH 3-7 as a mobile phase A, and ethanol as a mobile phase B, to obtain a purified sample solution; and c. nanofiltrating the purified sample solution with a membrane concentration device, and freeze drying it in a vacuum freeze drier, to obtain a purified β-nicotinamide mononucleotide.

In the method for purifying β-nicotinamide mononucleotide, the microfiltration membrane used for microfiltration in Step a has a pore size of 0.2-1 μm.

In the method for purifying β-nicotinamide mononucleotide, the nanofiltration membrane used for nanofiltration in Step a has a 200 molecular weight cut-off.

In the method for purifying β-nicotinamide mononucleotide, the nanofiltration membrane used for nanofiltration in Step a is a hollow fiber membrane.

In the method for purifying β-nicotinamide mononucleotide, the concentration of the crude product solution concentrated in Step a is 20-30 g/L.

In the method for purifying β-nicotinamide mononucleotide, the concentration of the purified sample solution after nanofiltration with a membrane concentration device in Step c is 100-150 g/L.

In the method for purifying β-nicotinamide mononucleotide, the volume ratio of the mobile phase A to the mobile phase B in Step b is 2:98-1:1.

In the method for purifying β-nicotinamide mononucleotide, the nanofiltration membrane used for nanofiltration in Step c is a hollow fiber membrane with a 200 molecular weight cut-off.

In the method for purifying β-nicotinamide mononucleotide, the elution time for gradient elution in Step b is 40 min.

Beneficial Effect

By purifying β-nicotinamide mononucleotide by preparative high performance liquid chromatography on octadecylsilane-bonded silica gel in the present invention, the purity of β-nicotinamide mononucleotide can be up to 98%, the yield can be up to 80% or more, and the production efficiency is increased by over 2 times compared with other processes, thus effectively solving the problem of difficulty in complete removal of other analogues having similar charges and polarities during the purification process of β-nicotinamide mononucleotide.

DETAILED DESCRIPTION

A preferred embodiment of a method for purifying β-nicotinamide mononucleotide according to the present invention comprises the steps of:

S100: sequentially microfiltrating and nanofiltrating a pretreated β-nicotinamide mononucleotide solution with membrane concentration devices, to collect a concentrated crude product solution;

S200: adjusting the obtained crude product solution to pH 3-7, loading it onto a preparative reverse phase high performance liquid chromatographic column, and purifying by gradient elution using an octadecylsilane-bonded silica gel as a stationary phase, a hydrochloric acid solution at pH 3-7 as a mobile phase A, and ethanol as a mobile phase B, to obtain a purified sample solution; and S300: nanofiltrating the purified sample solution with a membrane concentration device, and freeze drying it in a vacuum freeze drier, to obtain a purified β-nicotinamide mononucleotide.

In the present invention, β-nicotinamide mononucleotide, a substrate for synthesizing coenzyme I, is purified by reverse phase high performance liquid chromatography, using a octadecylsilane-bonded silica gel a stationary phase, and a hydrochloric acid solution and ethanol as mobile phases, and then further concentrated and freeze dried, to obtain purified β-nicotinamide mononucleotide. The method for purifying β-nicotinamide mononucleotide according to the present invention is simple in operation, and can effectively remove other analogues having similar charges and polarities, such that the prepared β-nicotinamide mononucleotide has a high purity, a high yield, and a large output. Therefore, the method is applicable to large-scale production in industry.

Preferably, the microfiltration membrane used for microfiltration in Step S100 has a pore size of 0.2-1 μm. Specifically, the microfiltration membrane used for microfiltration in Step S100 in the present invention has a pore size of 0.5 μm.

The fundamental principle underlying microfiltration is sieving. Particles with a particle size of 10 μm or greater are filtered off under a differential static pressure. Under an operation pressure of 0.7-7 bar, the solvent in the raw solution penetrates through the micropores on the membrane and flows to a low pressure side of the membrane under the differential pressure, and the particles with a particle size larger than the pore size of the membrane is retained, thereby realizing the separation of particles from the solvent in the raw solution. The mechanism of retaining the particles by microfiltration is sieving. The separation effect of the membrane depends on the physical structure and the pore shape and size of the membrane.

Where the microfiltration membrane used for microfiltration in an embodiment of the present invention has a pore size of 0.5 μm, large microorganisms and particles in the crude β-nicotinamide mononucleotide product solution can be preliminarily removed. The microfiltration membrane allows macromolecules and dissolved solid (inorganic) salts to pass through, but retains suspended matter, bacteria, and high molecular weight colloids, thereby achieving the preliminary purification for the crude β-nicotinamide mononucleotide product solution. If the pore size of the microfiltration membrane is too large, large microorganisms and particles may penetrate through the microfiltration membrane, thus affecting the effect of preliminary filtration. If the pore size is too small, β-nicotinamide mononucleotide may be caused to fail to penetrate through the microfiltration membrane, leading to the loss of the product.

Moreover, the nanofiltration membrane used for nanofiltration in Step S100 in the present invention has a 200 molecular weight cut-off. Further, in a preferred embodiment of the present invention, a nanofiltration membrane having a pore size of 1.5 nm is used, by which materials with a molecular weight of 200 or above can be retained.

More preferably, the nanofiltration membrane used for nanofiltration in Step S100 is a hollow fiber membrane.

Nanofiltration is a filtration method that permits the solvent molecules, some small molecular weight solutes, or low valence ions to penetrate through, and is characterized by having a high salt removal performance and capability to retain materials with a molecular weight of several hundreds under a quite low pressure. In the present invention, a nanofiltration membrane having a pore size of 1.5 nm and a 200 molecular weight cut-off is used, whereby the materials with a molecular weight of 200 or above are filtered off, to preliminarily filter off the impurities contained in β-nicotinamide mononucleotide. Moreover, by using a hollow fiber membrane as the nanofiltration membrane, the phosphate residue and other small molecular weight impurities produced during the process for preparing β-nicotinamide mononucleotide can be effectively removed due to the self-supporting effect resulting from the fibrous appearance of the hollow fiber membrane, whereby β-nicotinamide mononucleotide is further purified.

After microfiltration and nanofiltration, a concentrated crude product solution is collected, which has a concentration of 20-30 g/L.

In a preferred embodiment of the present invention, the concentration of the phosphoric acid solution or the hydrochloric acid solution in Step S200 is 2-5 wt %, and the concentration of the ethanol solution is 5-30 wt %.

More preferably, the phosphoric acid solution or the hydrochloric acid solution in Step S200 is used in an amount (by volume) of 5-20 ml of the phosphoric acid solution or the hydrochloric acid solution per ml of the sample solution, and the ethanol solution is used in an amount (by volume) of 100-400 ml of the ethanol solution per L of the mobile phases.

Specifically, if the mass concentration of the phosphoric acid solution or the hydrochloric acid solution is too high, washing off is caused during the gradient elution; and if the mass concentration is too low, the separation and purification effect of the material is affected. In the present invention, high degree of purification of β-nicotinamide mononucleotide can be achieved with the use of 2-5 wt % phosphoric acid solution or hydrochloric acid solution without washing off during the gradient elution.

Moreover, varying amount of acid may have an impact on the peak shape, thus affecting the detection effect. In an embodiment of the present invention, the phosphoric acid solution or the hydrochloric acid solution is used in an amount (by volume) of 5-20 ml of the phosphoric acid solution or the hydrochloric acid solution per ml of the sample solution, and the ethanol solution is used in an amount (by volume) of 100-400 ml of the ethanol solution per L of the mobile phases, such that the peak shape is symmetric and the tailing is reduced.

In a preferred embodiment of the present invention, adjusting the obtained crude production to pH 3-7 in Step S200 is conducted by adding a phosphoric acid solution or hydrochloric acid solution into the crude β-nicotinamide mononucleotide product solution obtained in the previous step S100 which is then loaded onto a preparative reverse phase high performance liquid chromatographic column where the mobile phase A is a hydrochloric acid solution at pH 3-7, and the mobile phase B is ethanol.

Specifically, during the reverse phase high performance liquid chromatography, generally a non-polar stationary phase (e.g. C18, or C8) is used, and the mobile phase is water or a buffer solution, to which methanol, ethanol, isopropanol, acetone, tetrahydrofuran and other organic solvents that are miscible with water are usually added to adjust the retention time. These are suitable for the separation of non-polar or weakly polar compounds. The pH affects the existing state of the sample, and thus affects the retention time of the sample. In an embodiment of the present invention, a hydrochloric acid solution at pH 3-7 and ethanol are used as the mobile phases, such that the retention time of the sample is effectively adjusted, and the time from the entering of the sample into the chromatographic column to existing the chromatographic column is optimized, thereby leading to a good separation effect for the sample. If the retention time of the sample is too long, the detection sensitivity is lowered; and if the retention time of the sample is too short, the effect of separating the β-nicotinamide mononucleotide from the impurities is decreased, thus influencing the purification of the β-nicotinamide mononucleotide.

The pH value of the mobile phase is controlled between 2 and 8. When the pH value is greater than 8, the carrier silica gel, that is, the stationary phase, is dissolved. When the pH value is less than 2, the phase chemically bonded to the silica gel is easy to fall off due to hydrolysis. In an embodiment of the present invention, the pH value is 3-7. In this case, the β-nicotinamide mononucleotide can exist stably with no destruction to its internal structure, and the separation effect of the sample is optimized. More preferably, the pH value of the mobile phase is 5 in the present invention, at which the purification effect of the sample is the most desirable.

In Step S200 in the present invention, the obtained crude product solution is adjusted to pH 3-7 with a phosphoric acid solution or a hydrochloric acid solution, because the crude product solution of β-nicotinamide mononucleotide still contains a phosphate residue; and a solution formulated with hydrochloric acid is used as the mobile phase A. In the present invention, no new impurities are introduced by adjusting the pH value of the crude product solution with a phosphoric acid solution or a hydrochloric acid solution, and the phosphate and others can be removed in the purification process.

Preferably, in an embodiment of the present invention, the volume ratio of the mobile phase A to the mobile phase B in Step S200 is 2:98-1:1.

The ratio of the mobile phases has an influence on the detection and purification effects of the sample. If the amount of the hydrochloric acid solution is increased and the amount of ethanol is decreased, the retention time of the sample is extended, and the sample is well separated. However, the sample peak detected is widened, and the peak height is reduced, thus affecting the detection sensitivity. If the amount of the hydrochloric acid solution is decreased and the amount of ethanol is increased, the detection sensitivity of the sample is high, but the separation effect of the sample is poor. In view of the nature of the sample and the purification conditions in the present invention, the hydrochloric acid solution at pH 3-7 and ethanol are used at a volume ratio of 2:98-1:1, such that the detection sensitivity of the sample is increased while the sample is well separated and purified.

Furthermore, in a preferred embodiment of the present invention, the elution time in gradient elution is 40 min. In particular, the purification is carried out by eluting with a gradient of 2% to 10% B.

Compared with isocratic elution, the use of gradient elution can provide a peak that is more symmetric and has no tailing, and can improve the column efficiency and the detection sensitivity. Furthermore, an elution time of 40 min allows the sample to have a suitable retention time, so that a most desirable separation and purification may be achieved for the β-nicotinamide mononucleotide.

In the present invention, β-nicotinamide mononucleotide, a substrate for synthesizing coenzyme I is initially purified by reverse phase high performance liquid chromatography, through which the problems occurring to the conventional ion exchange method of low purification efficiency, incapability to separate analogues having similar properties such as polarities to β-nicotinamide mononucleotide, and low yield are overcome.

The present invention is further explained with reference to specific examples.

In the present invention, chromatographic columns with a specification (column diameter*length): 5 cm*30cm, 15 cm*30 cm, and 30 cm*30 cm are used.

The column temperature is room temperature.

EXAMPLE I

1. Concentration of Crude Product:
A pretreated β-nicotinamide mononucleotide solution was sequentially microfiltrated and nanofiltrated with membrane concentration devices, where the microfiltration was carried out for removing microorganisms, and a hollow fiber membrane with a 200 molecular weight cut-off was used for nanofiltration. As a result, the crude product was concentrated to 20-30 g/L.

2. Purification:
Purification conditions:
Chromatographic column: column diameter and length 5 cm*30 cm;
Stationary phase: octadecylsilane-bonded silica gel;
Mobile phases: Phase A: hydrochloric acid solution at pH 3; and Phase B: ethanol;
Flow rate: 50-80 ml/min;
Detection wavelength: 260 nm;
Gradient: B%: 2%-12% (over 40 min); and
Amount of injection: 8-10 g.
Purification process: The concentrated crude product solution was adjusted to pH 3-7 with a phosphoric acid solution or a hydrochloric acid solution. The chromatographic column was rinsed with 30% or above of ethanol, equilibrated, and injected with the sample in an amount of 8-10 g. The sample was eluted for 40 min with a linear gradient, and the target peak was collected.

3. Concentration and Freeze Drying:
The purified sample solution was concentrated to 100-150 g/L by nanofiltrating using a membrane concentration device (a hollow fiber membrane with a 200 molecular weight cut-off), and then freeze dried in a vacuum freeze drier, to obtain β-nicotinamide mononucleotide with a purity that is higher than 98% and a total yield that can be up to 81.3%.

EXAMPLE II

1. Concentration of Crude Product:
A pretreated β-nicotinamide mononucleotide solution was microfiltrated and nanofiltrated with membrane concentration devices, where the microfiltration was carried out for removing microorganisms, and a hollow fiber membrane with a 200 molecular weight cut-off was used for nanofiltration. As a result, the crude product was concentrated to 20-30 g/L.

2. Purification:
Purification conditions:
Chromatographic column: column diameter and length 15 cm*30 cm;
Stationary phase: octadecylsilane-bonded silica gel;
Mobile phases: Phase A: hydrochloric acid solution pH 5; and Phase B: ethanol;
Flow rate: 400-500 ml/min;
Detection wavelength: 260 nm;
Gradient: B%: 2%-12% (over 40 min); and
Amount of injection: 60-80 g.
Purification process: The concentrated crude product solution was adjusted to pH 3-7 with a phosphoric acid solution or a hydrochloric acid solution. The chromatographic column was rinsed with 30% or above of ethanol, equilibrated, and injected with the sample in an amount of 60-80 g. The sample was eluted for 40 min with a linear gradient, and the target peak was collected.

3. Concentration and Freeze Drying:

The purified sample solution was concentrated to 100-150 g/L by nanofiltrating using a membrane concentration device (a hollow fiber membrane with a 200 molecular weight cut-off), and then freeze dried in a vacuum freeze drier, to obtain β-nicotinamide mononucleotide with a purity that is higher than 98% and a total yield that can be up to 82.3%.

EXAMPLE III

1. Concentration of Crude Product:

A pretreated coenzyme II solution was microfiltrated and nanofiltrated with membrane concentration devices, where the microfiltration was carried out for removing microorganisms, and a hollow fiber membrane with a 200 molecular weight cut-off was used for nanofiltration. As a result, the crude product was concentrated to 20-30 g/L.

2. Purification:

Purification conditions:

Chromatographic column: column diameter and length 30 cm*30 cm;

Stationary phase: octadecylsilane-bonded silica gel;

Mobile phases: Phase A: hydrochloric acid solution at pH 7; and Phase B: ethanol;

Flow rate: 2500-3000 ml/min;

Detection wavelength: 260 nm;

Gradient: B%: 2%-12% (over 40 min); and

Amount of injection: 350-400 g.

Purification process: The concentrated crude product solution was adjusted to pH 3-7 with a phosphoric acid solution or a hydrochloric acid solution. The chromatographic column was rinsed with 30% or above of ethanol, equilibrated, and injected with the sample in an amount of 350-400 g. The sample was eluted for 40 min with a linear gradient, and the target peak was collected.

3. Concentration and freeze drying:

The purified sample solution was concentrated to 100-150 g/L by nanofiltrating using a membrane concentration device (a hollow fiber membrane with a 200 molecular weight cut-off), and then freeze dried in a vacuum freeze drier, to obtain β-nicotinamide mononucleotide with a purity that is higher than 98% and a total yield that can be up to 80.9%.

In the present invention, a target peak of the sample is collected, and nanofiltrated with a membrane concentration device when a standard is met, followed by freeze drying in a vacuum freeze drier, to obtain purified β-nicotinamide mononucleotide. The freeze dried β-nicotinamide mononucleotide product prepared following the method of the present invention has a purity that is up to 98% and a total yield that can be up to 80% or above. The method of the present invention is simple in operation, and thus the production efficiency is increased by over 2 times compared with other processes, thereby effectively solving the problems existing in the prior art of difficulty in removal of phosphate residue, and low purity and low yield of the prepared product. The present invention has a promising prospect in the market, and is applicable to the production and purification of β-nicotinamide mononucleotide in industry.

It should be understood that the present invention is not limited to the embodiments above, and equivalent replacements or changes may be made by those ordinarily skilled in the art based on the description, which are all embraced in the protection scope as defined by the accompanying claims of the present invention.

What is claimed is:

1. A method for preparative purification of a salt of β-nicotinamide mononucleotide, comprising:
   a. sequentially microfiltrating and nanofiltrating a crude product solution containing β-nicotinamide mononucleotide to obtain a concentrated crude product solution containing β-nicotinamide mononucleotide;
   b. adjusting the concentrated crude product solution to pH 3-7 to obtain a loading solution, loading the loading solution onto a preparative reverse phase high performance liquid chromatographic column, and purifying a salt of β-nicotinamide mononucleotide by gradient elution with an octadecylsilane-bonded silica gel as a stationary phase, a hydrochloric acid solution at pH 3-7 as a mobile phase A, and 100% ethanol as a mobile phase B obtain a purified sample solution containing β-nicotinamide mononucleotide; and
   c. concentrating the purified sample solution by nanofiltrating the purified sample solution to obtain a concentrated purified sample solution, and freeze drying the concentrated purified sample solution in a vacuum freeze drier to obtain a purified salt of β-nicotinamide mononucleotide.

2. The method according to claim 1, wherein a membrane for the microfiltrating in Step a has a pore size of 0.2-1 μm.

3. The method according to claim 1, wherein a membrane for the nanofiltrating in Step a has a 200 molecular weight cut-off.

4. The method according to claim 3, wherein the membrane for the nanofiltrating in Step a is a hollow fiber membrane.

5. The method according to claim 1, wherein the concentrated crude product solution in Step a contains 20-30 g/L of β-nicotinamide mononucleotide.

6. The method according to claim 1, wherein the concentrated purified sample solution in Step c is 100-150 g/L of β-nicotinamide mononucleotide.

7. The method according to claim 1, wherein a volume ratio of the mobile phase A to the mobile phase B in Step b is 2:98-1:1.

8. The method according to claim 1, wherein a nanofiltration membrane for the nanofiltrating in Step c is a hollow fiber membrane with a 200 molecular weight cut-off.

9. The method according to claim 1, wherein an elution time for the gradient elution in Step b is 40 min.

* * * * *